(12) United States Patent
Corbucci

(10) Patent No.: US 8,024,041 B2
(45) Date of Patent: ***Sep. 20, 2011

(54) CARDIAC RESYNCHRONIZATION VIA LEFT VENTRICULAR PACING

(75) Inventor: Giorgio Corbucci, Cento (IT)

(73) Assignee: Medtronic, Inc., Minneapolis, MN (US)

( * ) Notice: Subject to any disclaimer, the term of this patent is extended or adjusted under 35 U.S.C. 154(b) by 186 days.

This patent is subject to a terminal disclaimer.

(21) Appl. No.: 12/418,721

(22) Filed: Apr. 6, 2009

(65) Prior Publication Data

US 2009/0192562 A1 Jul. 30, 2009

Related U.S. Application Data

(63) Continuation of application No. 10/422,065, filed on Apr. 23, 2003, now Pat. No. 7,558,626.

(51) Int. Cl.
*A61N 1/362* (2006.01)
(52) U.S. Cl. .......................................................... 607/9
(58) Field of Classification Search ................. 607/9, 25
See application file for complete search history.

(56) References Cited

U.S. PATENT DOCUMENTS

| 5,330,511 | A  | * | 7/1994 | Boute | 607/25 |
| 5,507,782 | A  | * | 4/1996 | Kieval et al. | 607/9 |
| 7,558,626 | B2 | * | 7/2009 | Corbucci | 607/9 |
| 2004/0147966 | A1 | * | 7/2004 | Ding et al. | 607/9 |

* cited by examiner

*Primary Examiner* — Eric D. Bertram
(74) *Attorney, Agent, or Firm* — Reed A. Duthler

(57) ABSTRACT

The invention is directed to techniques for providing cardiac resynchronization therapy by synchronizing delivery of pacing pulses to the left ventricle with intrinsic right ventricular depolarizations. An implantable medical device measures an interval between an atrial depolarization and an intrinsic ventricular depolarization is measured. In various embodiments, the intrinsic ventricular depolarization may be an intrinsic right or left ventricular depolarization. The implantable medical device delivers pacing pulses to the left ventricle to test a plurality of pacing intervals. The pacing intervals tested may be within a range around the measured interval between the atrial depolarization and the intrinsic ventricular depolarization. One of the pacing intervals is selected based on a measured characteristic of an electrogram that indicates ventricular synchrony. For example, the pacing interval may be selected based on measured QRS complex widths and/or Q-T intervals. The implantable medical device paces the left ventricle based on the selected pacing interval.

4 Claims, 9 Drawing Sheets

CARDIAC RESYNCHRONIZATION VIA LEFT VENTRICULAR PACING

CROSS-REFERENCE TO RELATED APPLICATIONS

This application is a continuation of U.S. patent application Ser. No. 10/422,065 filed on Apr. 23, 2003 now U.S. Pat. No. 7,558,626. The disclosure of the above application is incorporated herein by reference.

FIELD OF THE INVENTION

The invention relates to medical devices and, more particularly, to implantable medical devices used for cardiac pacing.

BACKGROUND OF THE INVENTION

Many patients that suffer from congestive heart failure (CHF) develop a wide QRS complex resulting from a delayed activation of one of the ventricles in the heart, and inter- and/or intraventricular electrical-mechanical dysynchrony. This ventricular "dysynchrony" may be caused by dilation of the heart, which disrupts the conductive pathways and interferes with depolarization sequences. Ventricular dysynchrony may worsen heart failure symptoms.

In a classic case of ventricular dysynchrony, the right ventricle of the heart activates first, and the left ventricle activates at a later time. Delayed activation of the left ventricle may be caused by a particular disruption of the conductive pathways of the heart, referred to as a left bundle branch block (LBBB). A patient who has LBBB often experiences a reduction in cardiac output because of dysynchronous ventricular contraction. Moreover, in the case of LBBB, different regions within the left ventricle may not contract together in a coordinated fashion, further reducing cardiac output.

Patients having a wide QRS complex or having inter- and/or intraventricular electrical-mechanical dysynchrony often are treated with an implanted medical device, such as a pacemaker, that paces both ventricles. The implanted medical device senses or paces atrial contractions, waits a predetermined time (or atrioventricular (AV) delay) after each sensed or paced atrial contraction, and then paces both ventricles. The ventricles may be paced simultaneously, or one ventricle may be paced before another. This biventricular pacing is often referred to as cardiac resynchronization.

BRIEF SUMMARY OF THE INVENTION

The invention is directed to techniques for cardiac resynchronization. In particular, the invention is directed to techniques for synchronizing delivery of pacing pulses to the left ventricle with intrinsic right ventricular depolarizations. One exemplary situation in which the invention may be applied is the provision of cardiac resynchronization therapy to patients with left bundle branch block (LBBB) who have adequate atrial-right ventricular conduction. Implantable medical devices employing these techniques may provide a more physiological interval between atrial and ventricular contractions, in the sense that the interval between the atrial and ventricular contractions is a function of an intrinsic, rather than paced, depolarization of the right ventricle. Further, implantable medical device employing this technique may consume less power than conventional devices that provide cardiac resynchronization therapy by delivering pacing pulses to both the right and left ventricles.

In order to determine the proper timing for delivery of pacing pulses to the left ventricle, an implantable medical device according to the invention measures an interval between an intrinsic or paced atrial depolarization and an intrinsic ventricular depolarization. The intrinsic ventricular depolarization may be an intrinsic right or left ventricular depolarization. The implantable medical device delivers pacing pulses to the left ventricle to test a plurality of pacing intervals determined based on the measured interval. A pacing interval is the interval between an atrial depolarization and delivery of a pacing pulse to the left ventricle. The pacing intervals tested may be within a range around the measured interval.

One of the pacing intervals is selected based on a measured characteristic of an electrogram that indicates ventricular synchrony. For example, the pacing interval may be selected based on measured QRS complex widths and/or Q-T intervals. The pacing interval selected may be the tested pacing interval that provides the shortest QRS complex width or the longest Q-T interval. In some embodiments, the selected pacing interval may be an average of the interval that provides the shortest QRS complex width and the pacing interval that provides the longest Q-T interval.

The implantable medical device paces the left ventricle based on the selected pacing interval. The implantable medical device may determine a difference between the selected pacing interval and the measured interval between the atrial depolarization and the intrinsic ventricular depolarization, and pace the left ventricle based on the difference. For example, the intrinsic ventricular depolarization may be a right ventricular depolarization, and where the pacing interval is equal to the measured interval, i.e., the left ventricular pace should be delivered at the same time as the intrinsic right ventricular depolarization, the implantable medical device may pace the left ventricle upon detection of subsequent intrinsic right ventricular contractions.

Where the pacing interval is greater than the measured interval, i.e., the left ventricular pace should be delivered after the intrinsic right ventricular depolarization, the implantable medical device may pace the left ventricle based on a determined difference between pacing interval and the measured interval. In particular, the implantable medical device paces the left ventricle upon expiration of an interval that is initiated upon detection of subsequent intrinsic right ventricular depolarizations. The interval is equal to the determined difference between the selected pacing interval and the measured interval. Pacing the left ventricle based on the determined difference may allow an implantable medical device to maintain ventricular synchrony despite beat-to-beat changes in the interval between atrial depolarizations and intrinsic right ventricular depolarizations due to changes in patient activity level, medication, or the like.

Where the pacing interval is less than the measured interval, i.e., the left ventricular pace should be delivered before the intrinsic right ventricular depolarization, the implantable medical device may, in order to maintain ventricular synchrony despite beat-to-beat changes in the interval between atrial depolarizations and intrinsic right ventricular depolarizations, periodically determine a current interval between an atrial depolarization and an intrinsic right ventricular depolarization. The implantable medical device may then determine a current pacing interval based on the current measured interval. The current pacing interval may be the difference between the current measured interval and the previously determined difference between the previously determined pacing interval and the previous measured interval. The implantable medical device paces the left ventricle upon expiration of the current pacing interval, which is initiated upon detection of subsequent paced or sensed atrial depolarizations.

In some embodiments, an implantable medical device according to the invention may include electrodes capable of sensing electrical activity within and delivering pacing pulses to an atrium, a right ventricle, and a left ventricle of a heart. In some embodiments, an implantable medical device may not include or may not use electrodes in the right ventricle. In such embodiments, the implantable medical device may detect an interval between an atrial depolarization and an intrinsic left ventricular depolarization, test pacing intervals around the measured interval, and select a pacing interval based on QRS complex widths and/or Q-T intervals. In such embodiments, the implantable medical device may determine a difference between the measured interval and the selected pacing interval, periodically measure a current interval between an atrial depolarization and an intrinsic left ventricular depolarization, determine a current pacing interval based on the current measure interval and the difference, and pace according to the current pacing interval.

In one embodiment, the invention provides an implantable medical device to provide cardiac resynchronization therapy. The implantable medical device includes electrodes to detect electrical signals within and deliver pacing pulses to a heart of a patient and a processor. The processor measures an interval between an atrial depolarization of the heart and an intrinsic ventricular depolarization of the heart based on the detected signals. The processor controls delivery of pacing pulses to a left ventricle of the heart via the electrodes at pacing intervals determined based on the interval between the atrial depolarization and the intrinsic ventricular depolarization. The processor selects one of the pacing intervals based on an electrogram signal representing signals detected by the electrodes. The processor may control delivery of pacing pulses to the left ventricle based on the selected one of the pacing intervals.

In another embodiment, the invention is directed to a method for providing cardiac resynchronization therapy in which an interval between an atrial depolarization and an intrinsic ventricular depolarization is measured. Pacing pulses are delivered to a left ventricle of a heart at pacing intervals determined based on the interval between the atrial depolarization and the intrinsic ventricular depolarization. One of the pacing intervals is selected based on an electrogram signal that represents signals within the heart. Pacing pulses may be delivered to the left ventricle based on the selected one of the pacing intervals.

In still another embodiment, the invention provides a computer-readable medium that comprises program instructions. The program instructions cause a programmable processor to measure an interval between an atrial depolarization and an intrinsic ventricular depolarization. The instructions also cause a processor to control delivery of pacing pulses to a left ventricle of a heart at pacing intervals determined based on the interval between the atrial depolarization and the intrinsic ventricular depolarization. The instructions further cause a processor to select one of the pacing intervals based on an electrogram representing signals within the heart. The instructions may cause the processor to control delivery of pacing pulses to the left ventricle based on the selected one of the pacing intervals.

DETAILED DESCRIPTION OF THE INVENTION

Figure 1:
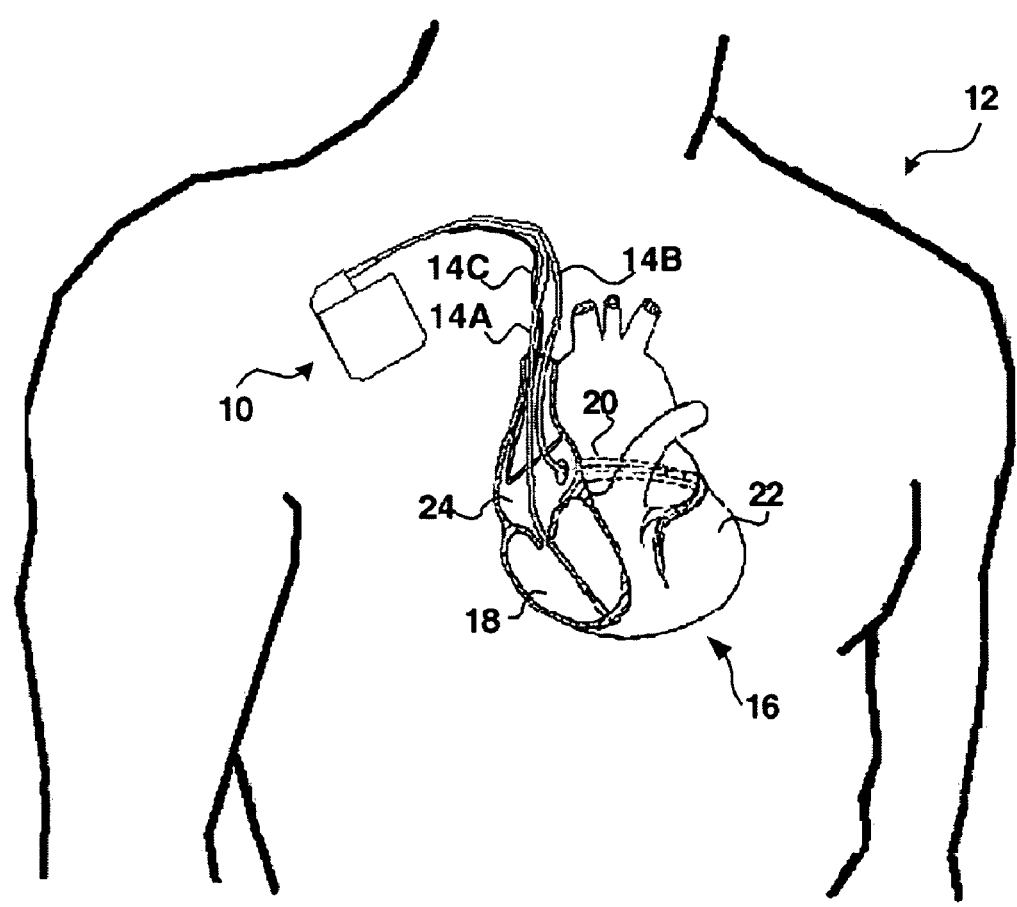
FIG. 1 is a conceptual diagram illustrating an exemplary implantable medical device implanted in a patient.

FIG. 1 is a conceptual diagram illustrating an exemplary implantable medical device (IMD) 10 implanted in a patient 12. IMD 10 may, as shown in FIG. 1, take the form of a multi-chamber cardiac pacemaker. In the exemplary embodiment illustrated in FIG. 1, IMD 10 is coupled to leads 14A, 14B and 14C (collectively "leads 14") that extend into the heart 16 of patient 12

More particularly, right ventricular (RV) lead 14A may extend through one or more veins (not shown), the superior vena cava (not shown), and right atrium 24, and into right ventricle 18. Left ventricular (LV) coronary sinus lead 14B may extend through the veins, the vena cava, right atrium 24, and into the coronary sinus 20 to a point adjacent to the free wall of left ventricle 22 of heart 16. Right atrial (RA) lead 14C extends through the veins and vena cava, and into the right atrium 24 of heart 16.

Each of leads 14 includes electrodes (not shown), which IMD 10 may use to sense electrical signals attendant to the depolarization and repolarization of heart 16, and to provide pacing pulses to heart 16. In some embodiments, IMD 10 may also provide cardioversion or defibrillation pulses via electrodes located on leads 14. The electrodes located on leads 14 may be unipolar or bipolar, as is well known in the art.

IMD 10 delivers cardiac resynchronization therapy to patient 12 via leads 14. In particular, as will be described in greater detail below, IMD 10 delivers pacing pulses to left ventricle 22 via lead 14B to synchronize contractions of left ventricle 22 with contractions of right ventricle 18 resulting from intrinsic depolarizations of right ventricle 18. One exemplary situation in which IMD 10 may be used is where patient 12 has left bundle branch block (LBBB), but has adequate physiological atrial-right ventricular conduction. By synchronizing contraction of ventricles 18 and 22 through pacing of left ventricle 22 alone, IMD 10 may provide a more physiological interval between atrial and ventricular contractions in the sense that the interval between the atrial and ventricular contractions is a function of an intrinsic, rather than paced, depolarization of the right ventricle. In addition, by pacing left ventricle 22 alone, IMD 10 may consume less power than conventional devices that provide cardiac resynchronization therapy by delivering pacing pulses to both the right ventricle 18 and left ventricle 22.

IMD 10 determines the timing of delivery of pacing pulses to left ventricle 22 based on one or more measured characteristics of an electrogram signal detected via one or more of leads 14 that represents electrical activity within heart 16. The measured characteristics indicate synchrony of contractions of ventricles 18 and 22. For example, wider QRS complex width indicates less synchronous contraction of ventricles 18 and 22. As another example, short Q-T intervals indicate increased sympathetic drive resulting from inadequate cardiac output, which in turn indicates dysynchrony of contraction of ventricles 18 and 22. Therefore, IMD 10 may, for example, select the left ventricular pace timing that results in the smallest QRS complex width, the largest Q-T interval, or the best combination of QRS complex width and Q-T interval.

The configuration of IMD 10 and leads 14 illustrated in FIG. 1 is merely exemplary. IMD 10 may be coupled to any number of leads 14 that extend to a variety of positions within or outside of heart 16. For example, in some embodiments, IMD 10 may not be coupled to a right ventricular lead 14A. Further, lead 14C may extend to the left atrium of heart 16.

Some of leads 14 may be epicardial leads. Some electrodes used by IMD 10 to sense electrical activity of heart 16 need not be carried by leads 14 at all, but may instead be integral with a housing of IMD 10 (not shown). Further, IMD 10 need not be implanted within patient 12, but may instead be coupled with subcutaneous leads 14 that extend through the skin of patient 12 to a variety of positions within or outside of heart 16.

Figure 2:
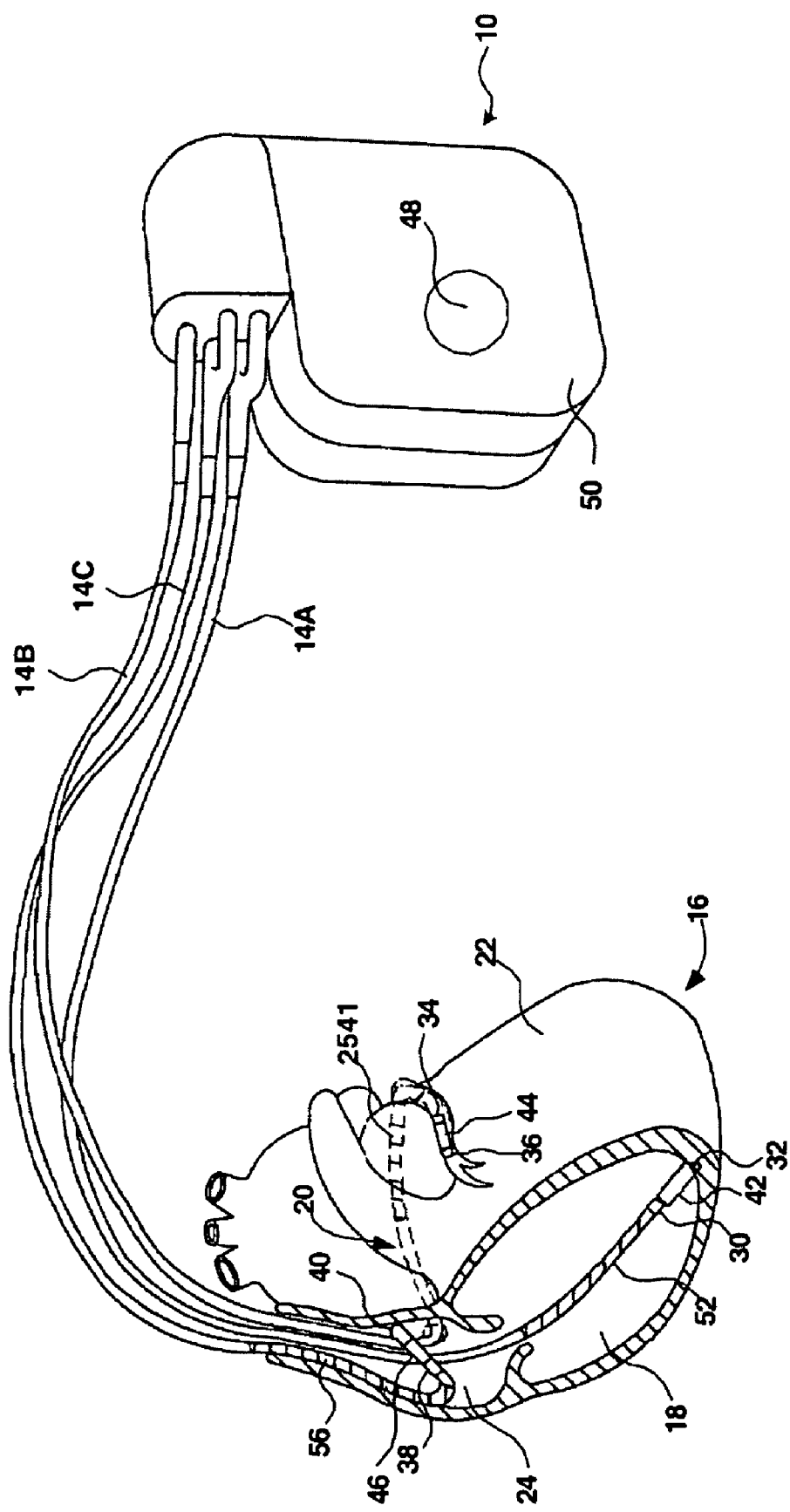
FIG. 2 is conceptual diagram further illustrating the implantable medical device of FIG. 1 and the heart of the patient.

FIG. 2 is conceptual diagram further illustrating IMD 10 and heart 16 of patient 12. Each of leads 14 may include an elongated insulative lead body carrying a number of concentric coiled conductors separated from one another by tubular insulative sheaths. Located adjacent distal end of leads 14A, 14B and 14C are bipolar electrodes 30 and 32, 34 and 36, and 38 and 40 respectively. Electrodes 30, 34 and 38 may take the form of ring electrodes, and electrodes 32, 36 and 40 may take the form of extendable helix tip electrodes mounted retractably within insulative electrode heads 42, 44 and 46, respectively. Each of the electrodes 30-40 is coupled to one of the coiled conductors within the lead body of its associated lead 14.

Sense/pace electrodes 30, 32, 34, 36, 38 and 40 sense electrical signals attendant to the depolarization and repolarization of heart 16. The electrical signals are conducted to IMD 10 via leads 14. Sense/pace electrodes 30, 32, 34, 36, 38 and 40 further may deliver pacing to cause depolarization of cardiac tissue in the vicinity thereof. IMD 10 may also include one or more indifferent housing electrodes, such as housing electrode 48, formed integral with an outer surface of the hermetically sealed housing 50 of IMD 10. Any of electrodes 30, 32, 34, 36, 38 and 40 may be used for unipolar sensing or pacing in combination with housing electrode 48.

Leads 14A, 14B and 14C may also, as shown in FIG. 2, include elongated coil electrodes 52, 54 and 56, respectively. IMD 10 may deliver defibrillation or cardioversion shocks to heart 16 via defibrillation electrodes 52-56. Defibrillation electrodes 52-56 may be fabricated from platinum, platinum alloy or other materials known to be usable in implantable defibrillation electrodes, and may be about 5 cm in length.

Figure 3:
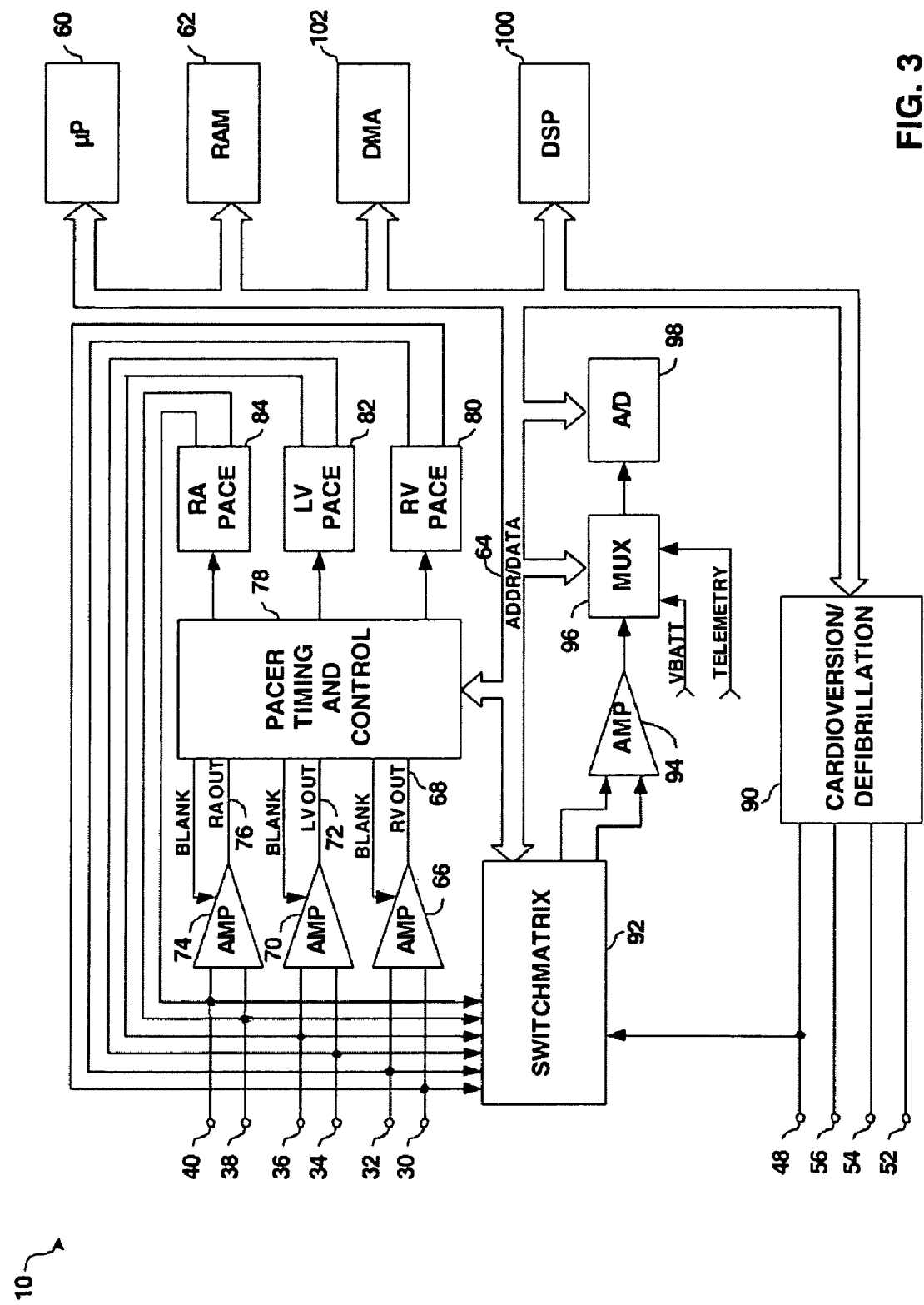
FIG. 3 is a functional block diagram of the implantable medical device of FIG. 1.

FIG. 3 is a functional block diagram of IMD 10. As shown in FIG. 3, IMD 10 may take the form of a multi-chamber pacemaker-cardioverter-defibrillator (PCD) having a microprocessor-based architecture. However, this diagram should be taken as exemplary of the type of device in which various embodiments of the present invention may be embodied, and not as limiting, as it is believed that the invention may be practiced in a wide variety of device implementations, including devices that provide cardiac resynchronization pacing therapies but do not provide cardioverter and/or defibrillator functionality.

IMD 10 includes a microprocessor 60. Microprocessor 60 may execute program instructions stored in a memory, e.g., a computer-readable medium, such as a ROM (not shown), EEPROM (not shown), and/or RAM 62. Program instruction stored in a computer-readable medium and executed by microprocessor 60 control microprocessor 60 to perform the functions ascribed to microprocessor 60 herein. Microprocessor 60 may be coupled to, e.g., to communicate with and/or control, various other components of IMD 10 via an address/data bus 64.

IMD 10 senses electrical activity within heart 16. Electrodes 30 and 32 are coupled to amplifier 66, which may take the form of an automatic gain controlled amplifier providing an adjustable sensing threshold as a function of the measured R-wave amplitude. A signal is generated on RV out line 68 whenever the signal sensed between electrodes 30 and 32 exceeds the present sensing threshold. Thus electrodes 30 and 32 and amplifier 66 may be used to detect intrinsic right ventricular depolarizations.

Electrodes 34 and 36 are coupled to amplifier 70, which also may take the form of an automatic gain controlled amplifier providing an adjustable sensing threshold as a function of measured R-wave amplitude. A signal is generated on LV out line 72 whenever the signal sensed between electrodes 34 and 36 exceeds the present sensing threshold. Thus, electrodes 34 and 36 and amplifier 70 may be used to detect intrinsic left ventricular depolarizations.

Electrodes 38 and 40 are coupled to amplifier 74, which may take the form of an automatic gain controlled amplifier providing an adjustable sensing threshold as a function of the measured P-wave amplitude. A signal is generated on RA out line 76 whenever the signal between electrodes 38 and 40 exceeds the present sensing threshold. Thus, electrodes 38 and 40 and amplifier 74 may be used to detect intrinsic atrial depolarizations.

IMD 10 paces heart 16. Pacer timing/control circuitry 78 preferably includes programmable digital counters which control the basic time intervals associated with modes of pacing. Circuitry 78 also preferably controls escape intervals associated with pacing. For example, IMD 10 may pace right atrium 24 via timing/control circuitry 78 triggering generation of pacing pulses by pacer output circuit 84, which is coupled to electrodes 38 and 40. Pacer timing/control circuitry 78 may trigger generation of pacing pulses for right atrium 24 upon expiration of an atrial escape interval.

As mentioned above, IMD 10 delivers pacing pulses to left ventricle 22 to synchronize contractions of left ventricle 22 with contractions of right ventricle 18 resulting from intrinsic depolarizations of right ventricle 18. Pacer timing/control circuitry 78 triggers generation of pacing pulses for left ventricle 22 by pacer output circuit 82, which is coupled to electrodes 34 and 36. As will be described in greater detail below, circuitry 78 triggers generation of pacing pulses delivered to left ventricle 22 upon expiration of an interval that may be timed from detection of either an atrial or intrinsic right ventricular depolarization.

IMD 10 may also provide biventricular modes of cardiac resynchronization therapy, or non-resynchronization pacing modalities that require delivery of pacing pulses to right ventricle 18, and may switch from a left ventricular cardiac resynchronization mode as described herein to one of these additional modes. Pacer timing/control circuitry 78 triggers generation of pacing pulses for right ventricle 18 by pacer output circuit 80, which is coupled to electrodes 30 and 32. Pacer timing/control circuitry 78 may trigger generation of pacing pulses for right ventricle 18 upon expiration of an A-V or V-V escape interval, depending on the pacing mode.

Output circuits 80, 82 and 84 may be pulse generation circuits known in the art, which include capacitors and switches for the storage and delivery of energy as a pulse. Pacer timing/control circuitry 78 resets escape interval counters upon detection of R-waves or P-waves, or generation of pacing pulses, and thereby controls the basic timing of cardiac pacing functions. Intervals defined by pacing circuitry 78 may also include refractory periods during which sensed R-waves and P-waves are ineffective to restart timing of escape intervals, and the pulse widths of the pacing pulses. The durations of these intervals are determined by microprocessor 60 in response to data stored in RAM 62, and are communicated to circuitry 78 via address/data bus 64. Pacer timing/control circuitry 78 also determines the amplitude of the cardiac pacing pulses under control of microprocessor 60.

Microprocessor 60 may operate as an interrupt driven device, and is responsive to interrupts from pacer timing/control circuitry 78 corresponding to the occurrence of sensed P-waves and R-waves and corresponding to the generation of cardiac pacing pulses. Those interrupts are provided via data/address bus 66. Any necessary mathematical calculations to be performed by microprocessor 60 and any updating of the values or intervals controlled by pacer timing/control circuitry 78 take place following such interrupts.

Microprocessor 60 determines the timing of delivery of pacing pulses to left ventricle 22, i.e., the intervals used to pacer timing/control circuit 78 to trigger generation of pacing pulses by output circuit 82, based on one or more measured characteristics, e.g., QRS complex width or Q-T interval, of one or more electrogram signals that represent electrical activity within heart 16. IMD 10 receives signals that represent electrical activity within heart 16, and may digitally process the signals to measure characteristics of the signals. Switch matrix 92 is used to select which of the available electrodes 30-40 and 48 are coupled to wide band (0.5-200 Hz) amplifier 94 for use in digital signal analysis. As will be described in greater detail below, any of a number of potential combinations of these electrodes may be used, so long as the signal provided by the combination allows for identification and measurement of the desired characteristic. Selection of electrodes is controlled by microprocessor 60 via data/address bus 66, and the selections may be varied as desired.

The analog signals derived from the selected electrodes and amplified by amplifier 94 are provided to multiplexer 96, and thereafter converted to a multi-bit digital signal by A/D converter 98. A digital signal processor (DSP) 100 may process the multi-bit digital signals to measure QRS complex widths and/or Q-T intervals, as will be described in greater detail below. In some embodiments, the digital signal may be stored in RAM 62 under control of direct memory access circuit 102 for later analysis by DSP 100.

Although IMD 10 is described herein as having separate processors, microprocessor 60 may perform both the functions ascribed to it herein and digital signal analysis functions ascribed to DSP 100 herein. Moreover, although described herein in the context of microprocessor based PCD embodiment IMD 10, the invention may be embodied in various implantable medical devices that include one or more processors, which may be microprocessors, DSPs, FPGAs, or other digital logic circuits. Further, in some embodiments, IMD 10 may not include or utilize DSP 100 to measure QRS complex widths and Q-T intervals. For example, IMD 10 may include analog slope or threshold detecting amplifier circuits to identify the beginning and end points of QRS complexes or Q-waves and T-waves, as is known in the art. In such embodiments of IMD 10, pacer timing/control circuit 78 may receive the output of these amplifier circuits, and provide an indication of the occurrence of these events to microprocessor 60 so that microprocessor may measure QRS complex widths and/or Q-T intervals.

IMD 10 may detect ventricular and/or atrial tachycardias or fibrillations of heart 16 using tachycardia and fibrillation detection techniques and algorithms known in the art. For example, the presence of a ventricular or atrial tachycardia or fibrillation may be confirmed by detecting a sustained series of short R-R or P-P intervals of an average rate indicative of tachycardia, or an unbroken series of short R-R or P-P intervals. IMD 10 is also capable of delivering one or more anti-tachycardia pacing (ATP) therapies to heart 16, and cardioversion and/or defibrillation pulses to heart 16 via one or more of electrodes 48, 52, 54 and 56.

Electrodes 48, 52, 54 and 56, are coupled to a cardioversion/defibrillation circuit 90, which delivers cardioversion and defibrillation pulses under the control of microprocessor 60. Circuit 90 may include energy storage circuits such as capacitors, switches for coupling the storage circuits to electrodes 48, 52, 54 and 56, and logic for controlling the coupling of the storage circuits to the electrodes to create pulses with desired polarities and shapes. Microprocessor 60 may employ an escape interval counter to control timing of such cardioversion and defibrillation pulses, as well as associated refractory periods.

Figure 4:
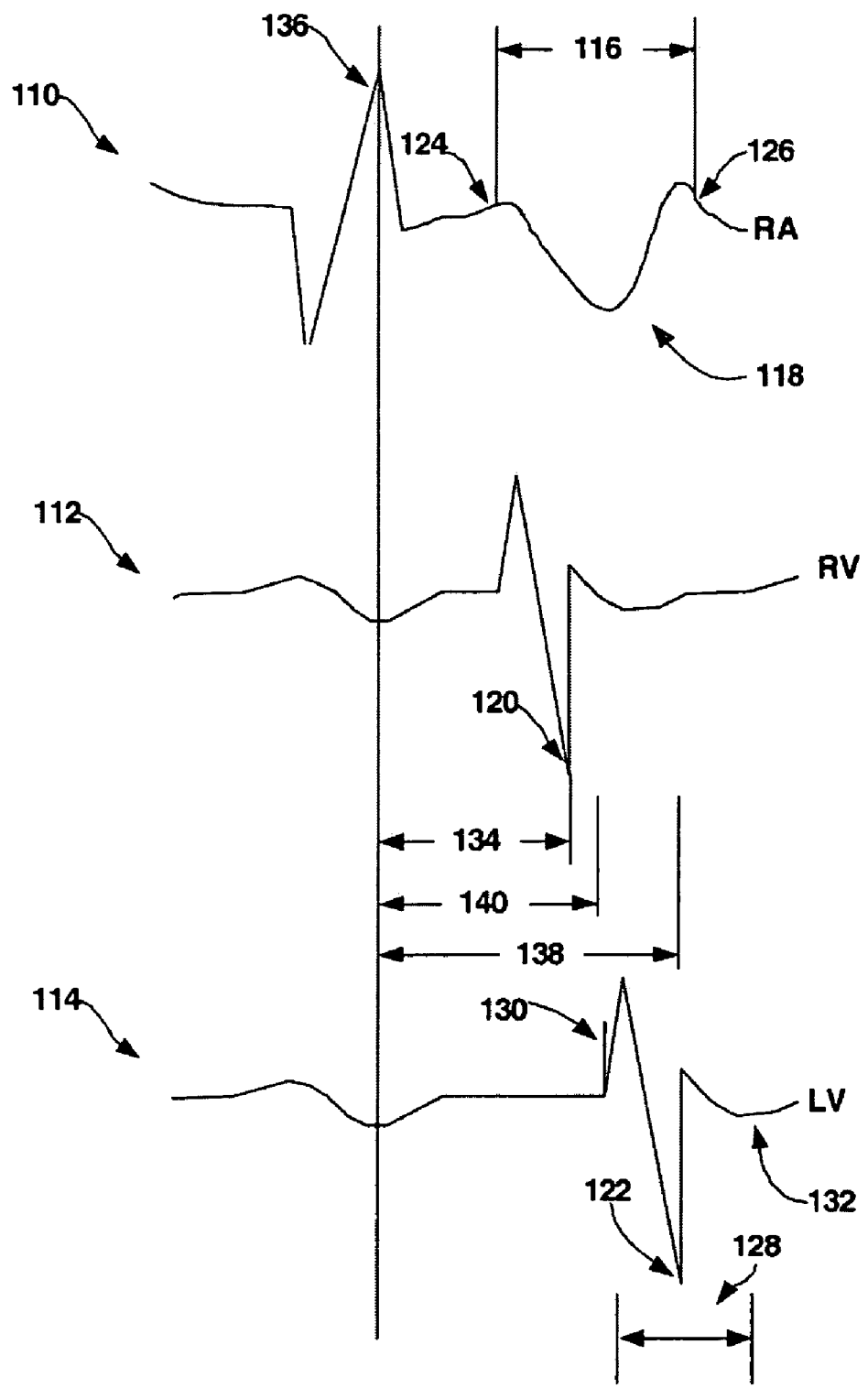
FIG. 4 is a timing diagram illustrating example electrogram (EGM) signals that represent electrical activity within the heart of the patient and illustrate techniques for determining left ventricular pace timing for cardiac resynchronization.

FIG. 4 is a timing diagram illustrating example electrogram (EGM) signals that represent electrical activity within heart 16. Signal 110 is a right atrial EGM. IMD 10 may digitally process atrial EGM 110 to measure a width 116 of QRS complex 118. Signal 110 may be detected using electrodes 38 and 40 of RA lead 14C in a bipolar configuration, or one of electrodes 38 and 40 and housing electrode 48 in a unipolar configuration.

In general, it is preferred that IMD 10 digitally process signals that include far-field QRS complexes 118, such as right atrial EGM 110, to measure widths 116. Processing these signals is preferred because such signals include QRS complexes that are more "global" in that they reflect depolarization of both ventricles 18, 22, and thus the widths 116 of far-field QRS complexes 118 more accurately reflect ventricular synchrony. In addition to atrial EGM signal 110, IMD 10 may detect signals that include far-field QRS complexes using two or more housing electrodes 48. Detecting cardiac signals via housing electrodes 48 may enable embodiments of IMD 10 that do not include an atrial lead.

In order to measure QRS complex width 116, DSP 100 first identifies far-field QRS complex 118 within signal 110. DSP 100 may identify QRS complex 118 within signal 110 by any methods known in the art. For example, DSP 100 may receive indications of the occurrence of an R-wave 120 or 122 from pacer timing/control circuit 78, and identify QRS complex 118 based on these indications. As another example, DSP 100 may identify QRS complex 118 by detecting a number of threshold-crossings of the digital signal provided by A/D converter 98, or zero-crossings of the first derivative of the digital signal occurring within a time window. As yet another example, DSP 100 may detect QRS complexes within signals 110-114 using techniques described in commonly assigned U.S. Pat. No. 6,029,087, to Wohlgemuth, and titled "Cardiac Pacing System With Improved Physiological Event Classification Based on DSP" ("Wohlgemuth '087 patent").

DSP 100 may measure width 116 as a period of time from a beginning point 124 to an ending point 126. DSP 100 may identify beginning point 124 and ending point 126 as threshold-crossings of the digital signal or zero-crossings of the first derivative of the digital signal.

Signals 112 and 114 are right and left ventricular EGMs, respectively, and may be detected via RV lead 14C and LV coronary sinus lead 14B, respectively. Signals 112 and 114 may be detected using bipolar electrode pairs 30, 32 and 34, 36, or one electrode from each pair and housing electrode 48 in a unipolar configuration.

IMD 10 may digitally process signal 114 to measure a Q-T interval 128. For example, DSP 100 may receive an indication of delivery of a pacing pulse 130 from pacer timing/control circuitry 78, and measure Q-T interval 128 as the period of time from pacing pulse 130 to detection of T-wave 132 within the digital signal provided by A/D converter 98. T-wave 132 may, for example, be detected using techniques described in the above-referenced Wohlgemuth '087 patent.

For ease of illustration, only a portion of each of EGM signals 110-114 representing a single cardiac cycle of heart 16 is shown in FIG. 4. However, it is understood that DSP 100 measures multiple QRS complex widths and/or Q-T intervals over multiple cardiac cycles. As will be described in greater detail below, DSP 100 measures these values in response to delivery of pacing pulses 130 to left ventricle 22. The values for QRS complex widths 116 and/or Q-T intervals 128 measured by DSP 100 may be stored in RAM 62 for later analysis by microprocessor 60. Microprocessor 60 analyzes the measured values to, for example, identify the smallest QRS complex width 116 or the largest Q-T interval 128.

In various embodiments of IMD 10, microprocessor 60 may measure intervals 134 between intrinsic and/or paced atrial depolarizations, e.g., P-waves 136, and intrinsic right ventricular depolarizations, e.g., R-waves 120. In other embodiments of IMD 10, microprocessor 60 may measure intervals 138 between P-waves 136 and intrinsic left ventricular depolarizations, e.g., R-waves 122. In either case, microprocessor 60 controls pacer timing/control circuitry 78 to test delivery of pacing pulses 130 at a variety of pacing intervals 140 timed from P-wave 136. Microprocessor 60 may control circuit to test pacing intervals 140 within a range around either interval 134 or interval 138, depending on the embodiment of IMD 10.

DSP 100 measures one or both of a QRS complex width 116 and Q-T interval 128 for each pacing interval 140 tested. Microprocessor 60 selects the tested pacing interval 140 that microprocessor 60 determines provides the best synchronization between contractions of right and left ventricles 18 and 22, e.g., the pacing interval 140 that resulted in the shortest QRS complex width 116, the longest Q-T interval 128, or the average of the pacing intervals 140 that resulted in the shortest QRS complex width 116 and the longest Q-T interval 128, respectively. Microprocessor 60 then controls delivery of pacing pulses to left ventricle 22 based on the selected pacing interval 140, as will be described in greater detail below.

Figure 5:
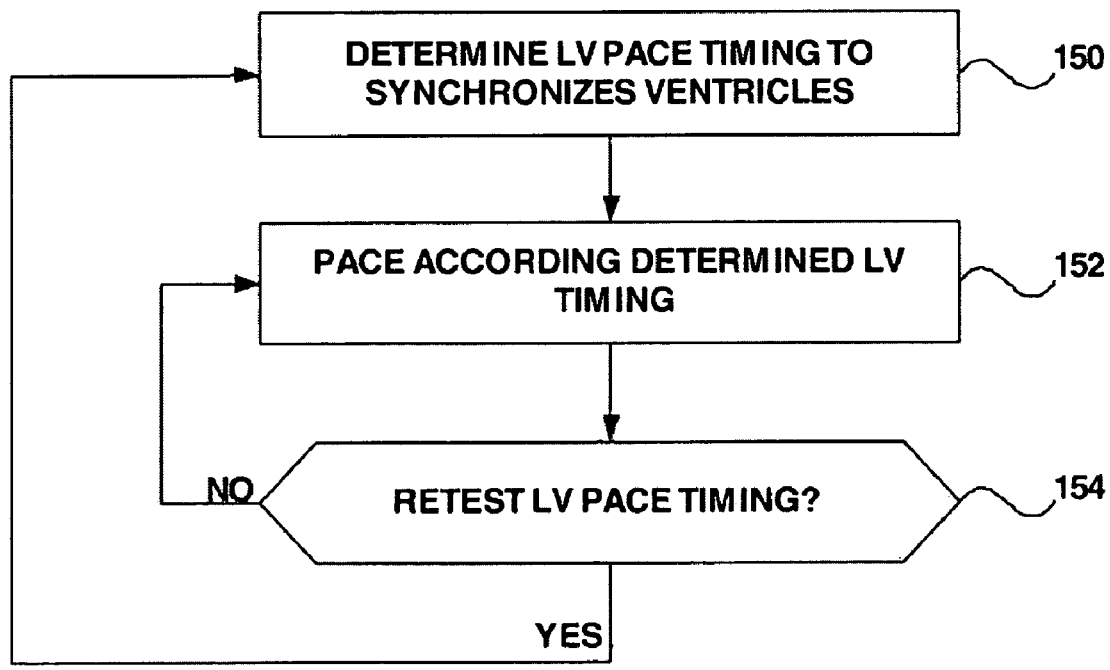
FIG. 5 is a flow diagram illustrating an example method that an implantable medical device may employ to deliver cardiac resynchronization therapy according to the invention.

FIG. 5 is a flow diagram illustrating an example method that IMD 10 may employ to deliver cardiac resynchronization therapy according to the invention. In general, IMD 10, and more particularly microprocessor 60 of IMD 10, determines a timing of left ventricular pacing that synchronizes the paced contractions of left ventricle 22 with contractions of right ventricle 18 resulting from intrinsic depolarizations of right ventricle 18 (150). Processor 60 determines the timing of left ventricular pacing based on measured characteristics of electrogram signals, e.g., QRS complex widths 16 and/or Q-T intervals 28. Processor 60 controls pacing of left ventricle 22 based on the determined timing (52). Processor 60 periodically retests the timing of left ventricular pacing, e.g., hourly, daily, or monthly, to account for longer-term changes in the condition of patient 12.

Figure 6:
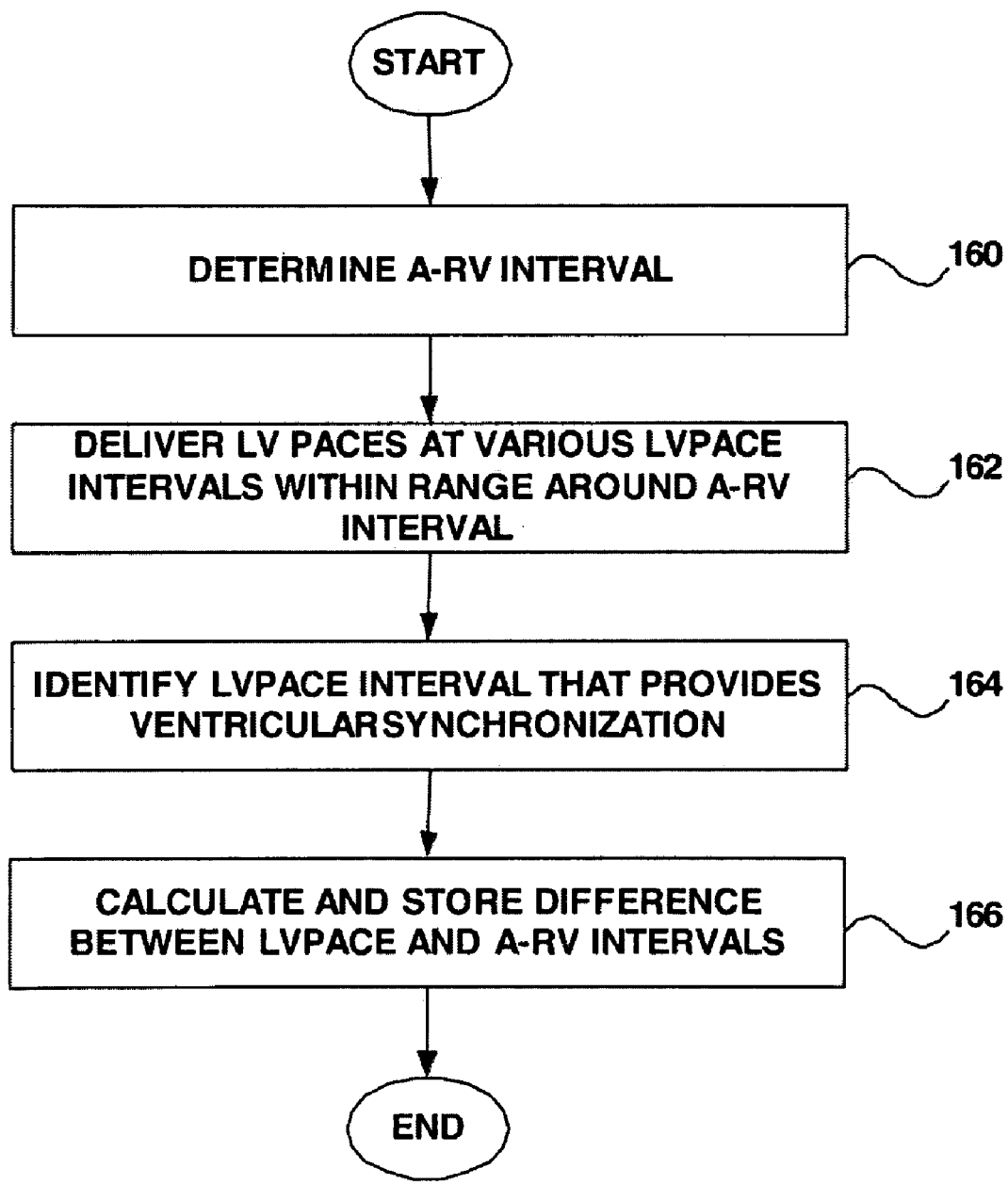
FIG. 6 is a flow diagram illustrating an example method that an implantable medical device may employ to determine left ventricular pace timing for cardiac resynchronization.
Figure 7:
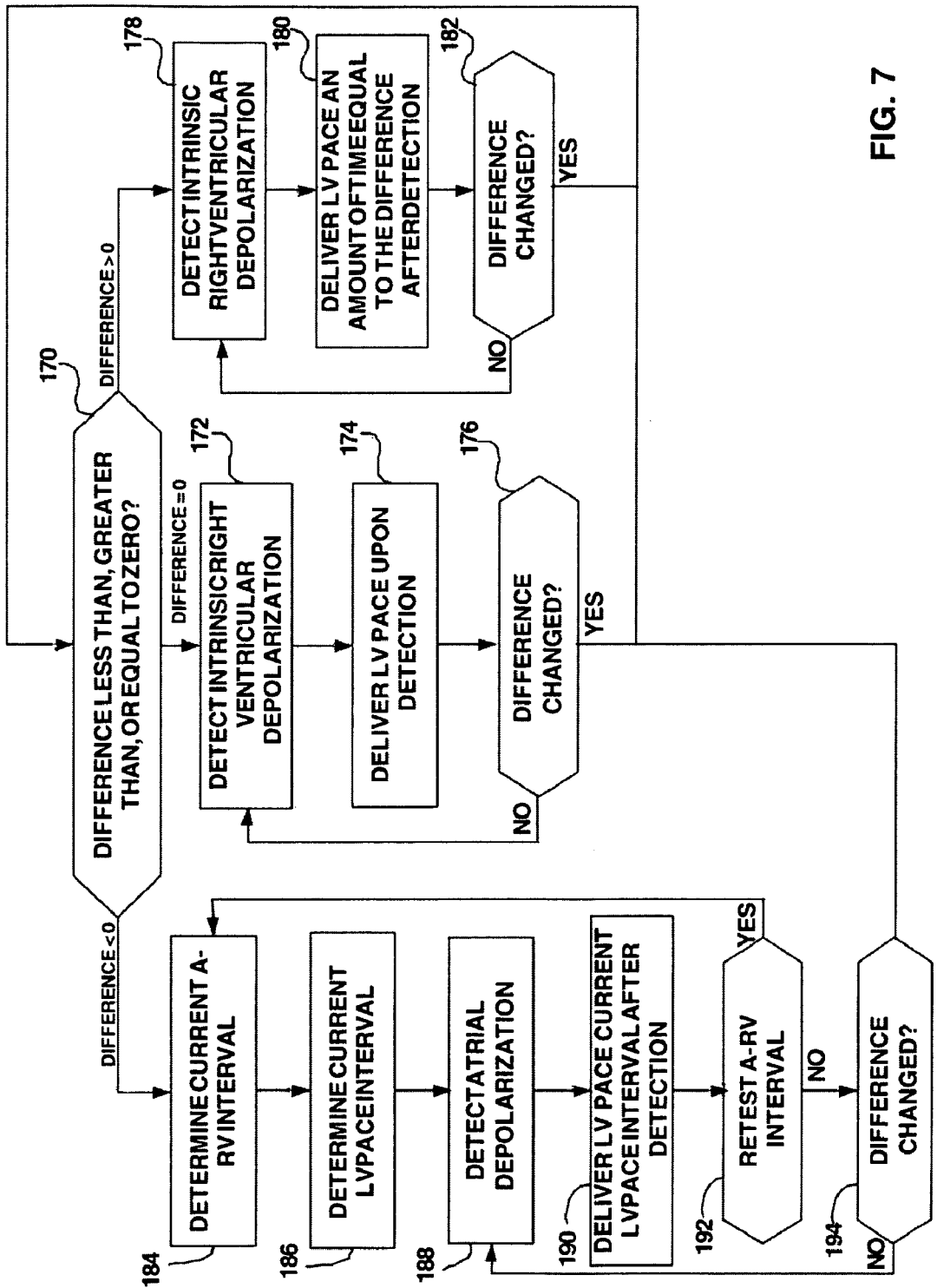
FIG. 7 is flow diagram illustrating an example method that an implantable medical device may employ to pace the left ventricle based on the determined timing.
Figure 8:
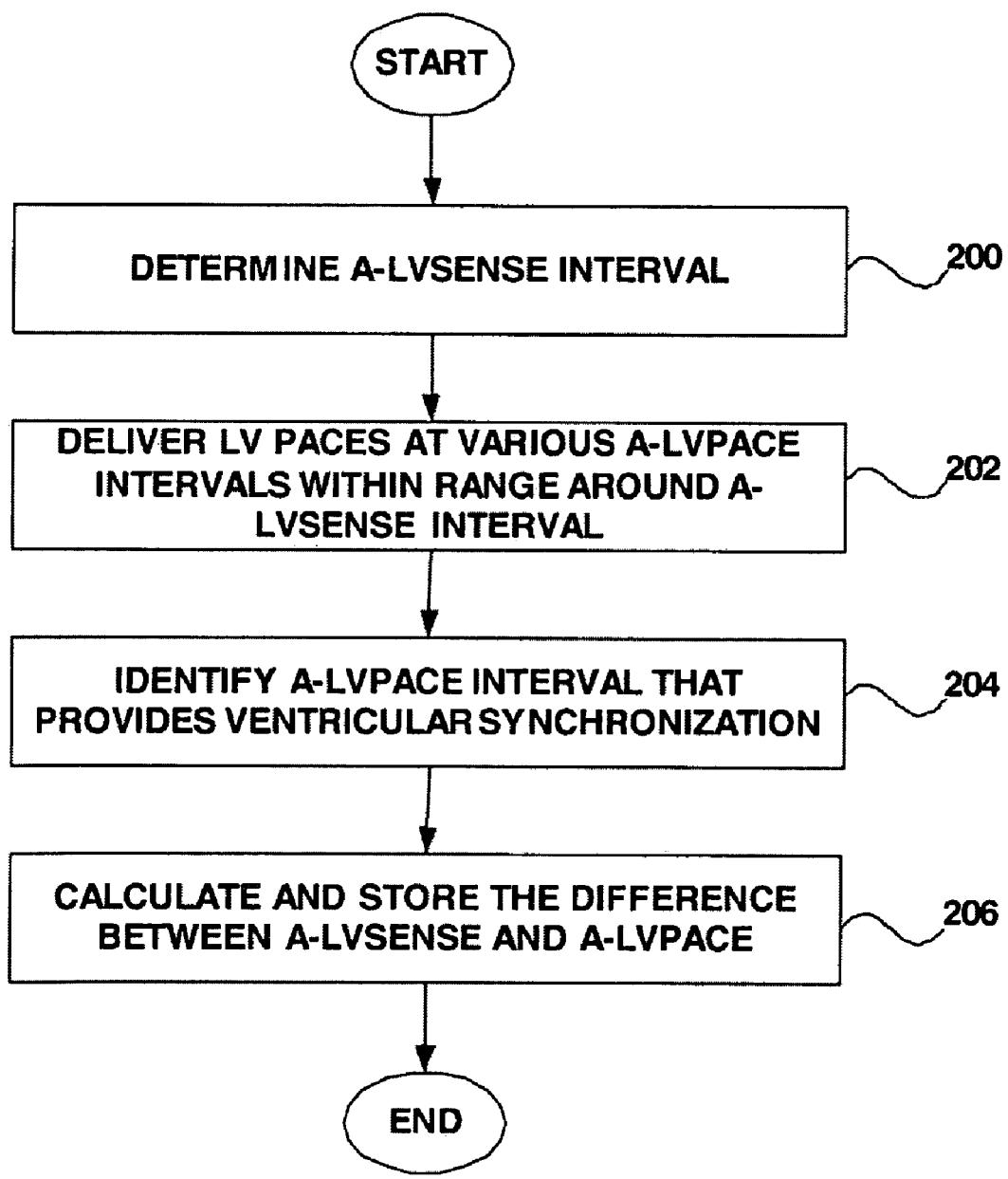
FIG. 8 is a flow diagram illustrating another example method that an implantable medical device may employ to determine left ventricular pace timing for cardiac resynchronization.

FIGS. 6-9 further illustrate the method of FIG. 5 according to various embodiments of the invention. In particular, FIGS. 6 and 8 illustrate methods that may be employed by IMD 10 to determine the timing of left ventricular pacing for synchronization with intrinsic right ventricular depolarizations. FIG. 6 illustrates a method that may be employed by IMD 10 to determine the timing based on a measured interval between an atrial depolarization and an intrinsic right ventricular depolarization, e.g., interval 134 (FIG. 4). FIG. 8 illustrates a method that may be employed by IMD 10 to determine the timing based on a measured interval between an atrial depolarization and an intrinsic left ventricular depolarization, e.g., interval 138 (FIG. 4).

Figure 9:
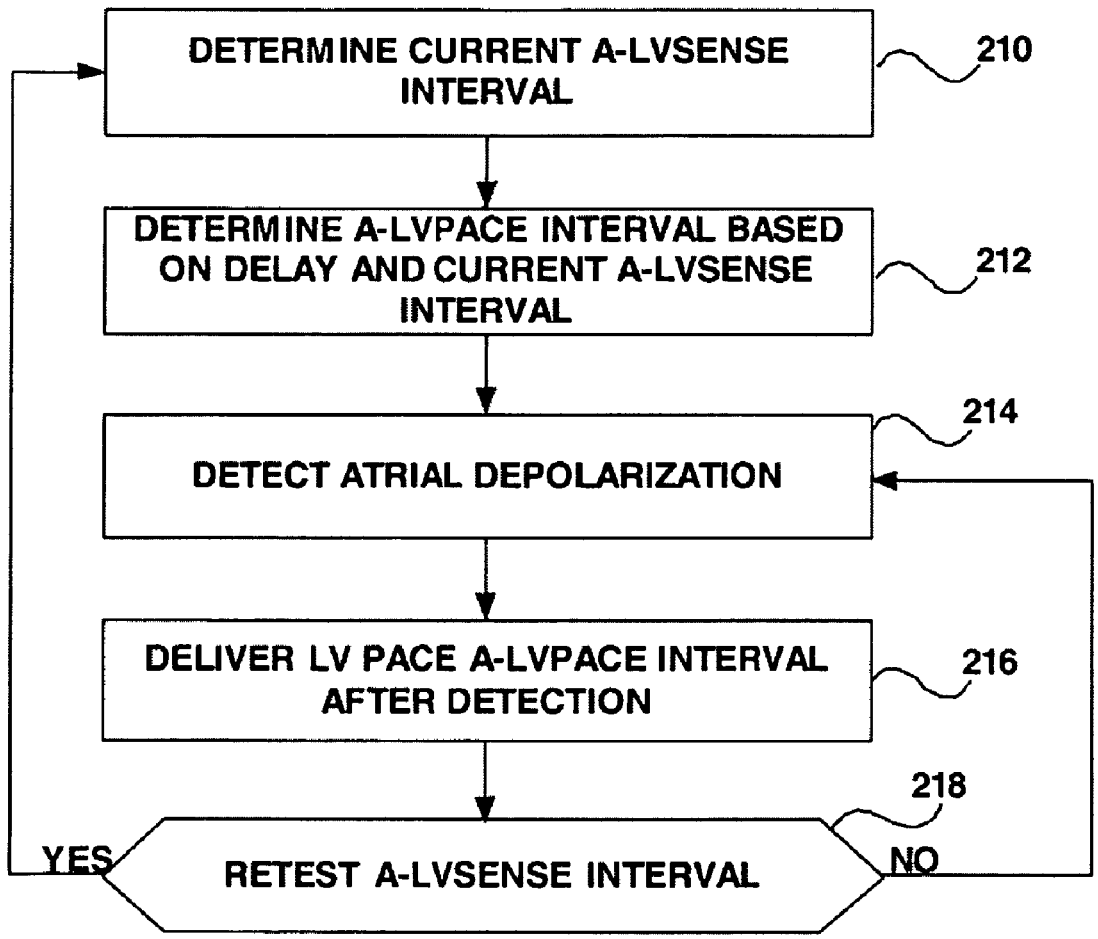
FIG. 9 is flow diagram illustrating another example method that an implantable medical device may employ to pace the left ventricle based on the determined timing.

The method illustrated in FIG. 6 may be applied in situations where IMD 10 is coupled to a right ventricular lead 14A that includes electrodes for sensing electrical activity in right ventricle 18, such as bipolar electrodes 30 and 32. The method illustrated in FIG. 8 may be applied whether or not IMD 10 is coupled to right ventricular lead 14A, requiring only that IMD 10 be coupled to left ventricular lead 14B for pacing and sensing left ventricle 22, e.g., via electrodes 34 and 36. FIGS. 7 and 9 illustrate methods for pacing left ventricle 22 based on the timing as determined according to the methods illustrated in FIGS. 6 and 8, respectively.

As shown in FIG. 6, IMD 10 measures an interval 134 between an intrinsic or pace atrial depolarization, e.g., P-wave 136, and an intrinsic right ventricular contraction, e.g. R-wave 120, as described above (160). In some embodiments, IMD 10 may measure a plurality of such A-RV intervals 134 and determine an average of the measured A-RV intervals. IMD 10 then delivers pacing pulses to left ventricle 22 at a variety of pacing intervals 140 measured from an intrinsic or paced P-wave 136 (162). IMD 10 may test pacing intervals 140 within a range around the determined A-RV interval 134.

IMD 10 then identifies the pacing interval 140 that provides synchronization of left ventricular pacing with intrinsic right ventricular contractions, as described above (164). As described above, IMD 10 may measure QRS complex widths 116 and/or Q-T intervals 128 corresponding to each pacing interval 140. IMD 10 selects one of the tested pacing intervals 140 based on the measured values. For example, IMD 10 may select the tested pacing interval 140 which results in the smallest QRS complex width 116 or longest Q-T interval 128. Where IMD 10 measures both, IMD 10 may select a pacing interval 140 by averaging the pacing intervals that resulted in the smallest QRS complex width 116 or longest Q-T interval 128, respectively.

IMD 10 calculates and stores the difference between the selected pacing interval 140 and the measured A-RV interval 134 (166) for use in pacing left ventricle 22, as will be described in greater detail with reference to FIG. 7. In some embodiments, A-RV intervals 134 may be measured and pacing intervals 140 may be tested individually for paced and intrinsic P-waves 136. In such embodiments, IMD 10 may calculate and store differences determined using each of paced and intrinsic P-waves 134, and apply the respective differences to pace left ventricle 22 depending on whether a paced or intrinsic P-wave 134 has been detected.

FIG. 7 illustrates a method that may be employed by IMD 10 to pace left ventricle 22 based on a calculated difference between the selected pacing interval 140 and the measured A-RV interval 134. If the difference is equal to zero (170), IMD 10 delivers pacing pulses to left ventricle 22 upon detection of intrinsic ventricular depolarizations, e.g., R-waves 120 (172, 174). If the difference is greater than zero (170), i.e., if the selected pacing interval 140 is greater than the measured A-RV interval 134, IMD 10 delivers pacing pulses to left ventricle 22 upon expiration of a counter initiated upon detection of intrinsic ventricular depolarizations, e.g., R-waves 120 (178, 180). The counter is set to measure an amount of time equal to the determined difference between the selected pacing interval 140 and the measured A-RV interval 134. Calculating the difference between the selected pacing interval 140 and the measured A-RV interval 134, and pacing left ventricle 22 based on the difference, as opposed to the selected pacing interval 140, allows IMD 10 to maintain ventricular synchrony despite beat-to-beat variation in the A-RV interval.

If the difference is less than zero (170), i.e., if pacing pulses must be delivered to left ventricle 22 prior to intrinsic ventricular depolarizations to provide ventricular synchrony, IMD 10 periodically determines a current A-RV interval 134 (184, 192), and determines a current pacing interval 140 as the sum of the current A-RV interval and the difference (186, 192). IMD 10 may determine current A-RV intervals and current pacing intervals every 10, 20, 32 or 100 cardiac cycles, for example.

IMD 10 delivers pacing pulses to left ventricle 22 the current pacing interval 140 after detection of a paced or intrinsic P-wave 136 (188, 190). Periodically determining current A-RV intervals and current pacing intervals allows IMD 10 to maintain ventricular synchrony despite beat-to-beat variation in the A-RV interval and despite the necessity of delivering pacing pulses to left ventricle 22 prior to intrinsic right ventricular depolarizations. As mentioned above, IMD 10 may periodically, e.g. hourly, weekly, or monthly, perform the method illustrated in FIG. 6 to recalculate the difference. Periodically recalculating the difference may allow IMD 10 to address longer-term changes in the condition of patient 12.

FIG. 8 illustrates a method that may be employed by IMD 10 to determine the timing based on a measured interval 138 between a paced or intrinsic atrial depolarization, e.g. a P-wave 136, and an intrinsic left ventricular depolarization, e.g., an intrinsic R-wave 122 (FIG. 4) (200). A single such A-LVSENSE interval 138 may be measured, or an average of several such A-LVSENSE intervals 138 may be determined.

IMD 10 then delivers pacing pulses to left ventricle 22 at a variety of pacing intervals 140 measured from an intrinsic or paced P-wave 136 (202). IMD 10 may test pacing intervals 140 within a range around the determined A-LVSENSE interval 138. IMD 10 identifies the pacing interval 140 that provides synchronization of left ventricular pacing with intrinsic right ventricular contractions, e.g., based on measured QRS complex widths 116 and/or Q-T intervals 128, as described above (204). IMD 10 calculates and stores a difference between the selected pacing interval 140 and the determined A-LVSENSE interval 138 (206). Separate intervals and differences may be determined for intrinsic and paced atrial depolarizations, as described above.

FIG. 9 illustrates a method that may be employed by IMD 10 to pace left ventricle 22 based on a calculated difference between a selected pacing interval 140 and the determined A-LVSENSE interval 138. IMD 10 periodically determines a current A-LVSENSE interval 138 (210, 218), and determines a current pacing interval 140 as the sum of the current A-LVSENSE interval and the difference (212, 218). IMD 10 may determine current A-RV intervals and current pacing intervals every 10, 20, 32 or 100 cardiac cycles, for example. IMD 10 delivers pacing pulses to left ventricle 22 upon expiration of a counter initiated upon detection of a paced or intrinsic P-wave 136 (214, 216). The counter is set to measure an amount of time equal to the determined current pacing interval 140.

A number of embodiments of the invention have been described. However, one skilled in the art will appreciate that the invention can be practiced with embodiments other than those disclosed. The disclosed embodiments are presented for purposes of illustration and not limitation, and the invention is limited only by the claims that follow.

What is claimed is:

1. A method for providing cardiac resynchronization therapy comprising:
    measuring an interval between an atrial depolarization and an intrinsic ventricular depolarization;
    delivering pacing pulses to a left ventricle of a heart at pacing intervals determined based on the measured interval between the atrial depolarization and the intrinsic ventricular depolarization;
    measuring a characteristic of an electrogram signal representing signals within the heart; and
    selecting one of the pacing intervals based on the measured characteristic of the electrogram signal representing signals within the heart,
    wherein measuring a characteristic of an electrogram comprises measuring a plurality of QRS complex widths, each of the QRS complex widths corresponding to a respective one of the delivered pacing pulses, and
    wherein selecting one of the pacing intervals comprises selecting one of the pacing intervals that corresponds to a smallest one of the QRS widths.

2. A method for providing cardiac resynchronization therapy comprising:
    measuring an interval between an atrial depolarization and an intrinsic ventricular depolarization;
    delivering pacing pulses to a left ventricle of a heart at pacing intervals determined based on the measured interval between the atrial depolarization and the intrinsic ventricular depolarization;
    measuring a characteristic of an electrogram signal representing signals within the heart; and
    selecting one of the pacing intervals based on the measured characteristic of the electrogram signal representing signals within the heart,
    wherein measuring a characteristic of an electrogram comprises measuring a plurality of Q-T intervals, each of the Q-T intervals corresponding to a respective one of the delivered pacing pulses, and
    wherein selecting one of the pacing intervals comprises selecting one of the pacing intervals that corresponds to a largest one of the Q-T intervals.

3. A non-transitory computer-readable medium comprising instructions that cause a processor to:
    measure an interval between an atrial depolarization and an intrinsic ventricular depolarization;
    control delivery of pacing pulses to a left ventricle of a heart at pacing intervals determined based on the measured interval;
    measure a characteristic of an electrogram signal representing the signals detected by the electrodes; and
    select one of the pacing intervals based on the measured characteristic of the electrogram signal representing the signals detected by the electrodes, wherein the instructions that cause a processor to measure a characteristic of an electrogram comprise instructions that cause a processor to measure a plurality of QRS complex widths within the electrogram, each of the QRS complex widths corresponding to a respective one of the delivered pacing pulses, and wherein the instructions that cause a processor to select one of the pacing intervals comprise instructions that cause a processor to select one of the pacing intervals that corresponds to a smallest one of the QRS widths.

4. A non-transitory computer-readable medium comprising instructions that cause a processor to:

measure an interval between an atrial depolarization and an intrinsic ventricular depolarization;

control delivery of pacing pulses to a left ventricle of a heart at pacing intervals determined based on the measured interval;

measure a characteristic of an electrogram signal representing the signals detected by the electrodes; and select one of the pacing intervals based on the measured characteristic of the electrogram signal representing the signals detected by the electrodes, wherein the instructions that cause a processor to measure a characteristic of an electrogram comprises instructions that cause a processor to measure a plurality of Q-T intervals within the electrogram, each of the Q-T intervals corresponding to a respective one of the delivered pacing pulses, and wherein the instructions that cause a processor to select one of the pacing intervals comprise instructions that cause a processor to select one of the pacing intervals that corresponds to a largest one of the Q-T intervals.

* * * * *